United States Patent

Zink et al.

[11] Patent Number: 4,705,775
[45] Date of Patent: Nov. 10, 1987

[54] RECORDING MATERIAL EMPLOYING CHROMOGENIC BISQUINAZOLINES

[75] Inventors: Rudolf Zink, Therwil; Ian J. Fletcher, Magden, both of Switzerland

[73] Assignee: Ciba-Geigy Corporation, Ardsley, N.Y.

[21] Appl. No.: 895,013

[22] Filed: Aug. 7, 1986

Related U.S. Application Data

[63] Continuation of Ser. No. 542,226, Oct. 14, 1983, Pat. No. 4,625,027.

[30] Foreign Application Priority Data

Oct. 25, 1982 [CH] Switzerland .................. 6201/82
Jun. 28, 1983 [CH] Switzerland .................. 3523/83

[51] Int. Cl.$^4$ .................. B41M 5/16; B41M 5/18; B41M 5/22
[52] U.S. Cl. .................. 503/218; 427/151; 503/217; 503/223
[58] Field of Search .................. 346/217, 218, 223; 427/150-152; 544/62, 105, 116, 119, 284

[56] References Cited

U.S. PATENT DOCUMENTS 4,435,003  3/1984  Fletcher .................. 428/914
4,480,096 11/1985  Fletcher .................. 544/284
4,562,449 12/1985  Balli et al. .................. 346/218
4,587,538  5/1986  Shanton et al. .................. 346/218

*Primary Examiner*—Bruce H. Hess
*Attorney, Agent, or Firm*—Edward McC. Roberts; Meredith C. Findlay

[57] ABSTRACT

Chromogenic bisquinazolines of the formula

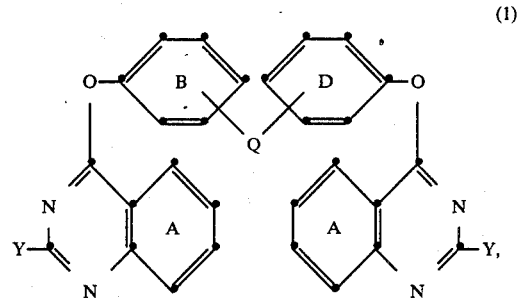

(1)

wherein
Q is the direct bond or an aliphatic or cycloaliphatic hydrocarbon radical, or is —CO—, —S— or —SO$_2$—, and
Y is the radical of a couplable compound, in particular an N-substituted 4-aminophenyl radical or a hydrogenated quinoline radical, and the rings A, B and D are unsubstituted or substituted by cyano, nitro, halogen, lower alkyl, phenyl, benzyl, lower alkoxy or lower alkoxycarbonyl.

These compounds are particularly suitable color formers for pressure-sensitive or heat-sensitive recording materials and produce intense yellow or orange colors of excellent fastness to light and, in particular, sublimation.

24 Claims, No Drawings

RECORDING MATERIAL EMPLOYING CHROMOGENIC BISQUINAZOLINES

This is a continuation of application Ser. No. 542,226 filed on Oct. 14, 1983, now U.S. Pat. No. 4,625,027.

The present invention relates to chromogenic bisquinazolines, to the preparation thereof, and to the use of these compounds as colour formers in pressure-sensitive or heat-sensitive recording materials.

The novel bisquinazolines have the general formula

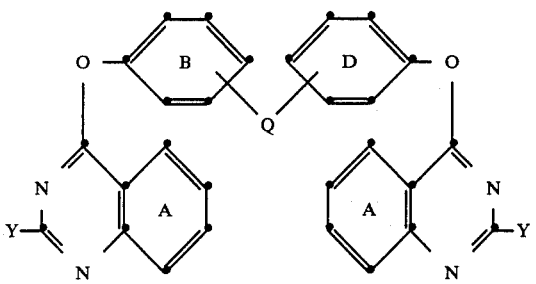

(1)

wherein

Q is the direct bond, an aliphatic or cycloaliphatic hydrocarbon radical containing not more than 8 carbon atoms, or is —CO—, —S— or —SO$_2$—, and Y is the radical of a couplable compound, and the rings A, B und D may each independently be unsubstituted or substituted by cyano, nitro, halogen, lower alkyl, phenyl, benzyl, lower alkoxy or lower alkoxycarbonyl.

In the definition of the radicals of the bisquinazolines of this invention, lower alkyl and lower alkoxy normally denote those groups or moieties of groups which contain 1 to 5, preferably 1 to 3, carbon atoms. Lower alkyl is e.g. methyl, ethyl, n-propyl, isopropyl, n-butyl, sec-butyl, tert-butyl, amyl or isoamyl, and lower alkoxy is e.g. methoxy, ethoxy, isopropoxy or tert-butoxy.

Q is preferably in the para-position with respect to both oxygen atoms.

Q as an aliphatic hydrocarbon radical is preferably an alkylene or alkylidene group. These groups may contain up to 8 carbon atoms and may have straight chain or branched chain configuration. The alkylene group preferably contains 1 to 4 carbon atoms and is e.g. the

—CH$_2$—, —CH$_2$CH$_2$—, —CH$_2$CH$_2$CH$_2$—,

—CH$_2$—CH—CH$_2$— or —CH$_2$CH$_2$CH$_2$CH$_2$—
　　　　|
　　　 CH$_3$ group. The alkylidene group is preferably ethylidene, propylidene, isopropylidene, butylidene or sec-butylidene. As a cycloaliphatic hydrocarbon radical, Q is e.g. the cyclopentylene group, the cyclohexylene group, the cyclopentylidene group or, preferably, the cyclohexylidene group. These cycloaliphatic radicals may contain one or two methyl groups.

Q is preferably the aliphatic or cycloaliphatic radical, in particular methylene or alkylidene of not more than 4 carbon atoms, and is most preferably isopropylidene, butylidene or cyclohexylidene.

Couplable compounds of which Y is a radical may be unsubstituted or N-mono-substituted or N,N-disubstituted anilines or naphthylamines, N-unsubstituted or N-substituted indoles, indolines, carbazoles, tetrahydrocarbazoles, dihydroquinolines, tetrahydroquinolines, dibenzylimides, benzomorpholines or phenylpyrazolines. Preferred couplable compounds are N,N-disubstituted anilines or N-substituted tetrahydroquinolines.

The monocyclic or polycyclic, carbocyclic or heterocyclic couplable compounds may also contain one or more ring substituents. Suitable C-substituents are e.g. halogens, hydroxyl, cyano, nitro, lower alkyl, lower alkoxy, lower alkoxycarbonyl, C$_1$–C$_8$acyl, preferably lower alkylcarbonyl, alkylene, cycloalkyl, benzyl or phenyl, whilst N-substituents are preferably C$_1$–C$_{12}$alkyl, C$_3$–C$_{12}$alkenyl or benzyl, each of which may also be substituted by e.g. cyano, halogen, nitro, hydroxyl, lower alkyl, lower alkoxy or lower alkoxycarbonyl.

The alkyl and alkenyl radicals may have straight chain or branched chain configuration and are e.g. methyl, ethyl, n-propyl, isopropyl, n-butyl, tert-butyl, sec-butyl, amyl, isoamyl, n-hexyl, 2-ethyl-hexyl, isooctyl, n-octyl, decyl or dodecyl, allyl, 2-methylallyl, 2-ethylallyl, 2-butenyl or octenyl.

Acyl is preferably formyl, lower alkylcarbonyl, e.g. acetyl or propionyl, or benzoyl. Further acyl radicals are lower alkylsulfonyl, e.g. methylsulfonyl or ethylsulfonyl, as well as phenylsulfonyl. Benzoyl and phenylsulfonyl may be substituted by halogen, methyl, methoxy or ethoxy.

The rings A, B and D are preferably not further substituted. If they do contain substituents, then each independently is substituted preferably by halogen, lower alkyl or lower alkoxy, e.g. by chlorine, methyl, isopropyl, tert-butyl or methoxy. Each benzene ring can advantageously contain 1 or 2 substituents. Preferred substituents of the benzene rings B and D are also methyl and tert-butyl as well as phenyl or benzyl.

Useful chromogenic bisquinazolines are those of the formula

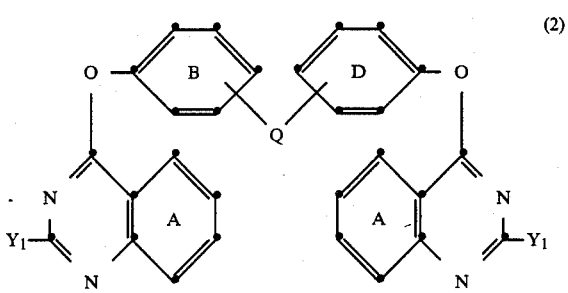

(2)

wherein
A, B, D and Q have the meanings assigned to them and Y$_1$ is an aminophenyl radical of the formula

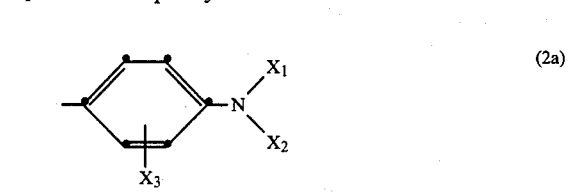

(2a)

or a hydrogenated heterocyclic radical of the formula

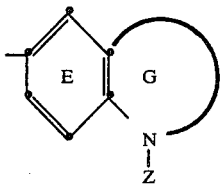 (2b)

wherein
- $X_1$ and $X_2$ are each independently hydrogen, $C_1$–$C_{12}$alkyl which is unsubstituted or substituted by halogen, hydroxyl, cyano or lower alkoxy, or are cycloalkyl, phenyl, benzyl, or phenyl or benzyl each substituted by halogen, nitro, cyano, lower alkyl, lower alkoxy or lower alkoxycarbonyl or
- $X_1$ and $X_2$, together with the nitrogen atom to which they are attached, are a 5- or 6-membered, preferably saturated, heterocyclic radical,
- $X_3$ is hydrogen, halogen, nitro, lower alkyl, lower alkoxy or lower alkoxycarbonyl, and
- Z is hydrogen or $C_1$–$C_8$alkyl which is unsubstituted or substituted by halogen, cyano or lower alkoxy, or is cycloalkyl or benzyl, and the ring E is unsubstituted or substituted by cyano, halogen, lower alkyl, e.g. methyl, or lower alkoxy such as methoxy, and the ring G is a hydrogenated 5- or 6-membered N-heterocyclic ring system which may contain a further hetero atom as ring member, e.g. oxygen, sulfur or nitrogen, and which is unsubstituted or C-substituted by a member or, depending on the substituents, by more than one, especially two, of the same or different members selected from halogen, cyano, hydroxyl, lower alkyl, lower alkoxy, $C_5$–$C_6$cycloalkyl, benzyl or $C_3$–$C_6$-alkylene.

Alkyl groups $X_1$ and $X_2$ may be straight chain or branched. Examples of such alkyl groups are methyl, ethyl, n-propyl, isopropyl, n-butyl, sec-butyl, amyl, isoamyl, n-hexyl, 2-ethyl-hexyl, n-octyl, isooctyl or n-dodecyl.

$X_1$ and $X_2$ as substituted alkyl groups are in particular cyanoalkyl, haloalkyl, hydroxyalkyl or alkoxyalkyl, each containing preferably a total of 2 to 4 carbon atoms, e.g. β-cyanoethyl, β-chloroethyl, β-hydroxyethyl, β-methoxyethyl, or β-ethoxyethyl.

$X_1$ and $X_2$ as cycloalkyl may be cyclopentyl or, preferably, cyclohexyl.

Preferred substituents of $X_1$ and $X_2$ as benzyl or phenyl are e.g. halogen atoms, cyano, methyl, methoxy or carbomethoxy. Examples of such araliphatic and aromatic radicals are methylbenzyl, chlorobenzyl, cyanophenyl, tolyl, chlorophenyl, methoxyphenyl or carbomethoxyphenyl.

A heterocyclic radical represented by $X_1$ and $X_2$, together with the nitrogen atom to which they are attached, is e.g. pyrrolidino, piperidino, pipecolino, morpholino, thiomorpholino or piperazino such as N-methylpiperazino. Preferred heterocyclic radicals —$NX_1X_2$ are pyrrolidino, piperidino or morpholino.

Each of $X_1$ and $X_2$ independently is preferably lower alkyl, benzyl, phenyl, lower alkylphenyl or lower alkoxyphenyl. $X_3$ is preferably hydrogen, chlorine, methyl, methoxy or ethoxy.

The ring E is preferably unsubstituted, but may with advantage contain a methyl group. The ring G is preferably 6-membered and C-substituted in particular by 1, 2 or 3 methyl groups.

Z is preferably lower alkyl, benzyl or β-cyanoethyl.

Preferred bisquinazolines of the formula (2) are those in which $Y_1$ is a radical of the formula (2a).

Valuable chromogenic bisquinazolines are those of the formula

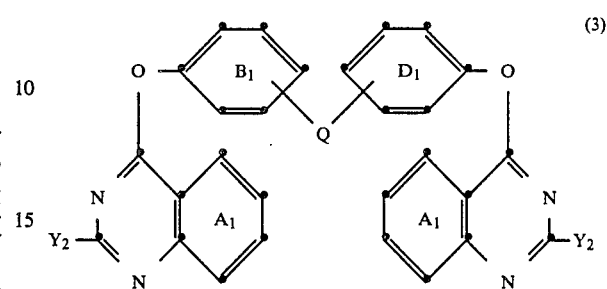 (3)

wherein
- $Q_1$ is the direct bond, a straight chain or branched alkylene or alkylidene radical, each containing not more than 8, preferably not more than 4, carbon atoms, or is the cyclohexylidene radical,
- $Y_2$ is
  an aminophenyl radical of the formula

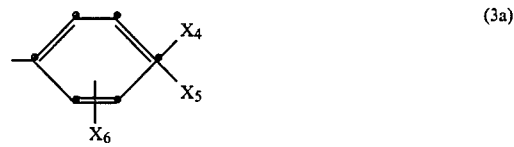 (3a)

a 5-indoline radical of the formula

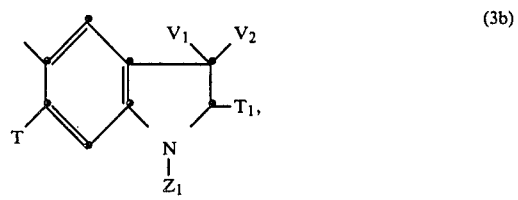 (3b)

a tetrahydroquinolinyl radical of the formula

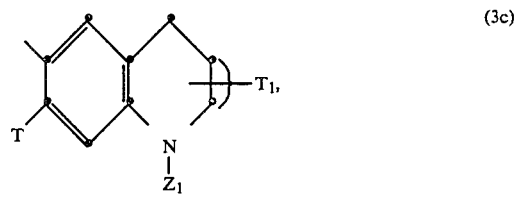 (3c)

a tetrahydroquinolinyl radical of the formula

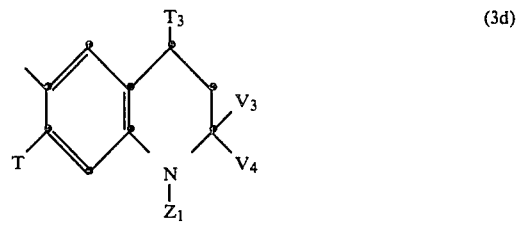 (3d)

or a benzomorpholino radical of the formula

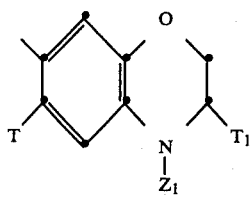

(3e)

in which formulae

X$_4$ and X$_5$ are each independently lower alkyl, cyanolower alkyl, benzyl, phenyl, lower alkylphenyl or lower alkoxyphenyl, or X$_4$ and X$_5$, together with the nitrogen atom to which they are attached, are pyrrolidino, piperidino or morpholino, X$_6$ is hydrogen, halogen, lower alkyl or lower alkoxy, Z$_1$ is hydrogen, C$_1$–C$_8$alkyl, C$_2$–C$_6$alkoxyalkyl, β-cyanoethyl or benzyl, T is hydrogen, halogen, lower alkyl, lower alkoxy, C$_1$–C$_4$acylamino or phenyl, T$_1$ and T$_2$ are each hydrogen, halogen, hydroxy, lower alkyl or lower alkoxy, and V$_1$, V$_2$, V$_3$ and V$_4$ are each hydrogen, lower alkyl, cycloalkyl or benzyl, or (V$_1$ and V$_2$) or (V$_3$ and V$_4$) are each together alkylene, and the rings A$_1$, B$_1$ and D$_1$ are each independently unsubstituted or substituted by one or two members of the group selected from cyano, halogen, lower alkyl, phenyl and lower alkoxy.

Preferred bisquinazolines of the formula (3) are those in which Y$_2$ is an aminophenyl radical of the formula (3a), wherein X$_4$ and X$_5$ are lower alkyl or benzyl. X$_6$ is preferably hydrogen. Q$_1$ is preferably in the para-position to the O-atoms and is preferably C$_1$–C$_4$alkylene or C$_2$–C$_4$alkylidene, in particular isopropylidene or butylidene. Q$_1$ is preferably also the cyclohexylidene radical. The ring A$_1$ is preferably unsubstituted. The benzene rings B$_1$ and D$_1$ are preferably unsubstituted or substituted by methyl and/or tert-butyl.

In the bisquinazolines of the formula (3), wherein Y$_2$ is a radical of the formula (3b), (3c), (3d) or (3e), the N-substituent Z$_1$ is preferably benzyl, β-cyanoethyl or C$_1$–C$_8$alkyl, e.g. n-octyl, n-butyl, isopropyl or, most preferably, methyl or ethyl. In these compounds of formula (3), Y$_2$ is preferably the tetrahydroquinolinyl radical of the formula (3d), T is preferably hydrogen or methyl, T$_1$ is preferably hydrogen, methyl, hydroxyl or chlorine, T$_2$ is preferably hydrogen, methyl or ethyl, V$_1$ and V$_2$ are preferably hydrogen or methyl, and V$_3$ and V$_4$ are preferably each lower alkyl and are most preferably each methyl.

Where (V$_1$ and V$_2$) or (V$_3$ and V$_4$) are each together alkylene, they preferably contain 4 or 5 carbon atoms and, together with the linking carbon atom, form a cyclopentane or cyclohexane ring.

Very interesting bisquinazolines are those of the formula

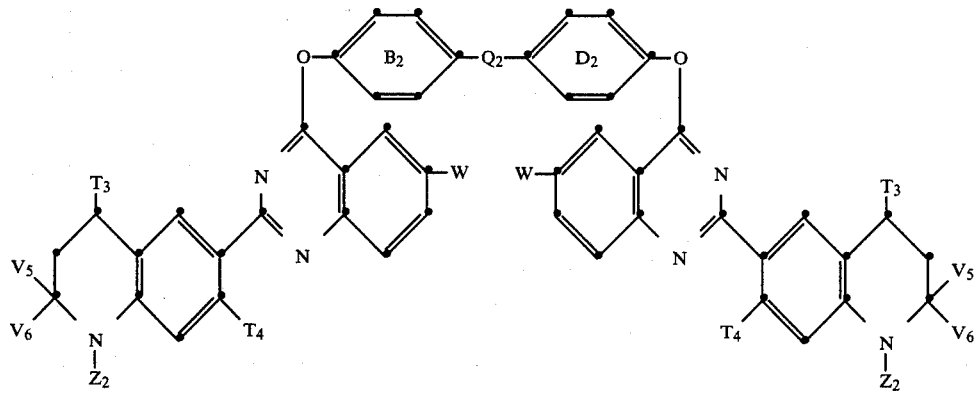

(4)

or, in particular, those of the formula

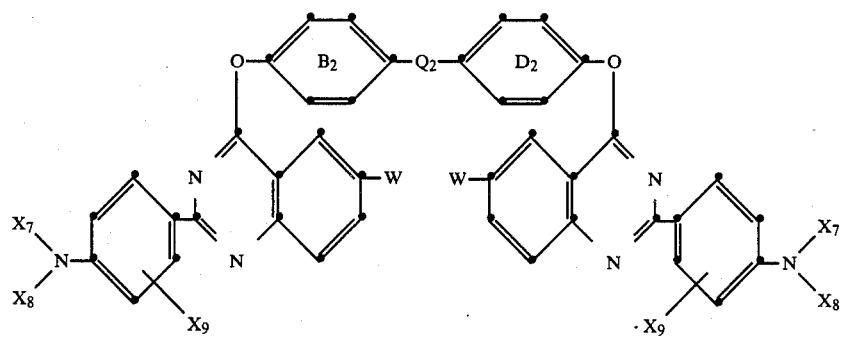

(5)

wherein

Q$_2$ is straight chain or branched alkylene or alkylidene each containing at most 4 carbon atoms, or is cyclohexylidene, X$_7$ and X$_8$ are each lower alkyl, β-cyanoethyl, benzyl or phenyl, or both together with the nitrogen atom are piperidino, X$_9$ is hydrogen, methyl, methoxy or ethoxy, Z$_2$ is C$_1$–C$_8$alkyl, β-cyanoethyl or benzyl, T$_3$, V$_5$ and V$_6$ are each lower alkyl, preferably methyl or ethyl, $T_4$ is hydrogen or methyl, and W is halogen, methyl, methoxy or preferably hydrogen, and the rings $B_2$ and $D_2$ are unsubstituted or substituted by one or two substituents selected from methyl, methoxy and tert-butyl.

The most preferred bisquinazolines are those of the formula (5), wherein $Q_2$ is butylidene or preferably isopropylidene. $X_7$ and $X_8$ are preferably benzyl or, most preferably, lower alkyl.

Halogen in compounds containing the above substituents in formulae (1) to (5) is e.g. fluorine, bromine or preferably chlorine.

The bisquinazolines of the formula (1) are prepared by reacting 1 mole of a bisphenol of the formula

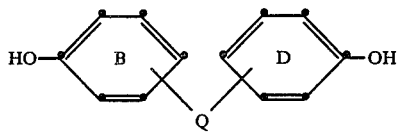
(6)

wherein B, D and Q have the meanings assigned to them, with 2 moles of a 4-haloquinazoline of the formula

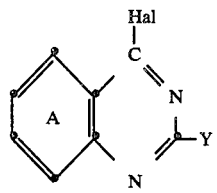
(7)

wherein A and Y have the meanings assigned to them and Hal is halogen, e.g. bromine, fluorine or preferably chlorine.

The reaction of the compounds of formula (6) with the compound of formula (7) is conveniently carried out in the presence of an acid acceptor, e.g. an alkali metal hydroxide, an alkali metal carbonate or a tertiary nitrogen base such as pyridine or a trialkylamine, and preferably also in the presence of a quaternary ammonium salt, e.g. tetrabutylammonium bromide, optionally in an organic solvent or in an aqueous organic two-phase medium and at reflux temperature.

Examples of suitable solvents are: cycloaliphatic or aromatic hydrocarbons, e.g. cyclohexane, benzene, toluene or xylene; chlorinated hydrocarbons such as chloroform, ethylene chloride or chlorobenzenes; ethers such as diethyl ether or glycol dimethyl ether; cyclic ethers such as dioxan or tetrahydrofuran; as well as dimethylformamide, diethylformamide, dimethylsulfoxide or acetonitrile.

Bisphenol compounds of the formula (6) which may be used as starting materials for the reaction with the quinzolines of the formula (7) are described e.g. in U.S. Pat. No. 3 244 550.

Representative examples of bisphenols used as starting materials of the formula (6) are: 2,4'-methylenediphenol, 4,4'-methylenediphenol, 2,2'-methylenediphenol, 4,4'-(1'',1''-butylidene)diphenol, 4,4'-sec-butylidenebiphenol, 4,4'-isopropylidenediphenol, 4,4'-isopropylidene-bis(2-methylphenol), 4,4'-cyclopentylidenediphenol, 4,4'-cyclohexylidenediphenol, 2,2'-methylene-di-p-cresol, 4,4'-methylenedi-o-cresol, 4,4'-methylene-bis(2-benzylphenol)-2,2'-methylene-bis(4-tert-butylphenol), 2,2'-methylene-bis(4-tert-pentylphenol), 2,2'-methylene-bis(4-chlorophenol), 4,4'-methylene-bis(2-chlorophenol), 4,4'-(1'''-methyl-n-hexylidene)diphenol, 4,4'-(1'',1''-butylidene)-bis(2-tert-butyl-5-methylphenol), 2,2'-methylene-bis(4-phenylphenol), 4,4'-methylene-bis(2-phenylphenol), 4,4'-thiodiphenol, 4,4'-sulfonyldiphenol, 2,2'-diphenol, 3,3'-diphenol, 4,4'-diphenol, 4,4'-dihydroxybenzophenone or 2,2'-dihydroxybenzophenone.

The starting materials of the formula (7) can be obtained by oxidising e.g. a 2-aminobenzamide of the formula

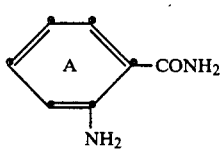
(8)

with an aldehyde of the formula $$Y-CHO \qquad (9)$$

to give a 1,2,3,4-tetrahydroquinazol-4-one of the formula

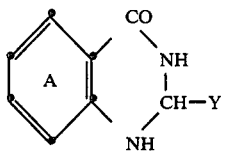
(10)

oxidising the compound of formula (10) to a compound of the formula

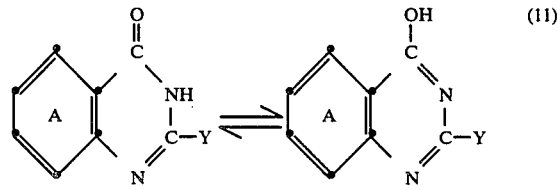
(11)

then replacing the hydroxyl group at the heterocyclic ring of the quinazoline system by a halogen atom, e.g. with phosphoroxy chloride in dichlorobenzene or with thionyl chloride in dimethylformamide, to give the starting compound of the formula (7). The 4-haloquinazoline so obtained can be further used without being isolated.

The oxidation of the reaction products of formula (10) to the 4-quinazolones of the formula (11) is carried out with an oxidising agent. Examples of suitable oxidising agents are chromates, bichromates, chlorates, chlorites, peroxides, e.g. hydrogen peroxide, manganese dioxide, lead dioxide, molecular oxygen, air, perborates, permanganates, nitrites, chlorine, bromine and, in particular, chloranil or bisulfites.

The best results with respect to yield and purity of the 4-quinazolones are obtained with chloranil as oxidising agent.

Carrying out the oxidation with sodium bisulfite is advantageous from the environmental point of view. Quinzolones of the formula (11) are obtained in good purity and yield using this oxidising agent in accordance with the method described in Synthesis 1981, (1), 35.

4-Haloquinazolines of the formula (7) and 4-quinazolones of the formula (11) and the preparation thereof are described e.g. in European published patent application 33716.

The bisquinazolines of the formulae (1) to (5) are normally colourless or, at most, faintly coloured. When these colour formers are brought into contact with a preferably acid developer, e.g. an electron acceptor, they produce intense yellow or orange shades of excellent fastness to sublimation and light. They are therefore also very useful when mixed with one or more other known colour formers, for example 3,3-(bis-aminophenyl)phthalides, 3-indolyl-3-aminophenylazaphthalides, 3,3-(bis-indolyl)phthalides, 3-aminofluoranes, 2,6-diaminofluoranes, leucoauramines, spiropyranes, spirodipyranes, chromenoidoles, phenoxazines, phenothiazines, carbazolylmethanes or other triarylmethaneleuco dyes, to give blue, grey or black colorations.

The bisquinazolines of the formulae (1) to (5) exhibit both on phenolic substrates, and especially on activated clays, an excellent colour intensity and fastness to sublimation and light. They are suitable in particular as rapidly developing colour formers for use in a heat-sensitive or especially in a pressure-sensitive recording material which can also be a copying material.

A pressure-sensitive material consists, for example, of at least one pair of sheets which contain at least one colour former of the formulae (1) to (5) dissolved in an orgaic solvent, and a solid electron acceptor as developer.

Typical examples of such developers are activated clays such as attapulgite, acid clay, bentonite, montmorillonite, activated clay, e.g. acid-activated bentonite or montmorillonite, and also zeolith, halloysite, silica, alumina, aluminium sulfate, aluminium phosphate, zinc chloride, activated kaolin or any clay. Preferred developers are acidic organic compounds, for example unsubstituted or ring-substituted phenols, salicylic acid or salicylates and their metal salts, or an acidic polymer, for example a phenolic polymer, an alkylphenolacetylene resin, a maleic acid/rosin resin or a partially or completely hydrolysed polymer of maleic acid and styrene, ethylene or vinyl methyl ether, or carboxypolymethylene. Mixtures of these polymers can also be used. Particularly preferred developers are acid clays, zinc salicylates or the condensation products of p-substituted phenols with formaldehyde. These latter may also contain zinc.

The developers may also be used in admixture with other basically inert or almost inert pigments, or with other auxiliaries such as silica gel or UB absorbers such as 2-(2-hydroxyphenyl)benzotriazoles. Examples of such pigments are: talcum, titanium dioxide, zinc oxide, chalk, clays such as kaolin, as well as organic pigments, e.g. urea/formaldehyde condensates (BET surface area of 2–75 g/m$^2$) or melamine/formaldehyde condensates.

The colour former effects a coloured marking at those points where it comes into contact with the electron acceptor. In order to prevent the colour formers contained in the pressure-sensitive recording material from becoming active prematurely, they are usually separated from the electron acceptor. This separation can conveniently be accomplished by incorporating the colour formers in foamlike, spongelike or honeycomblike structures. The colour formers are preferably encapsulated in microcapsules, which as a rule can be ruptured by pressure.

When the capsules are ruptured by pressure, for example with a pencil, the colour former solution is transferred to an adjacent sheet which is coated with an electron acceptor and a coloured area is thus produced. This colour results from the dye which is formed and which is absorbed in the visible range of the electromagnetic spectrum.

The colour formers are encapsulated preferably in the form of solutions in organic solvents. Examples of suitable solvents are preferably non-volatile solvents, for example a polyhalogenated paraffin, such as chloroparaffin, or a polyhalogenated diphenyl, such as monochlorodiphenyl or trichlorodiphenyl, and also tricresyl phosphate, di-n-butyl phthalate, dioctyl phthalate, trichlorobenzene, trichloroethylphosphate, an aromatic ether such as benzylphenyl ether, a hydrocarbon oil such as paraffin or kerosene, an alkylated (e.g. with isopropyl, isobutyl, sec- or tert-butyl) derivative of diphenyl, naphthalene or triphenyl; dibenzyl toluene, terphenyl, partially hydrogenated terphenyl, a benzylated xylene, a mono- or tetramethylated diphenylalkane or other chlorinated or hydrogenated, condensed aromatic hydrocarbons. Mixtures of different solvents, especially mixtures of paraffin oils or kerosene and diisopropylnaphthalene or partially hydrogenated terphenyl, are often used in order to obtain an optimum solubility for the colour formation, a rapid and intense coloration, and a viscosity which is advantageous for the microencapsulation.

The capsule walls can be formed evenly around the droplets of the colour former solution by coacervation; and the encapsulating material can consist of gelatin and gum arabic, as described e.g. in U.S. Pat. No. 2,800,457. The capsules can also be formed preferably from an aminoplast or a modified aminoplast by polycondensation, as described in British patent specifications Nos. 989 264, 1 156 725, 1 301 052 and 1 355 124. Also suitable are microcapsules which are formed by interfacial polymerisation, e.g. capsules formed from polyester, polycarbonate, polysulfonamide, polysulfonate, but in particular from polyamide or polyurethane.

The microcapsules containing the colour formers of the formulae (1) to (5) can be used for the production of a wide variety of known kinds of pressure-sensitive copying material. The various systems differ substantially from one another in the arrangement of the capsules, of the colour reactants, i.e. the developers, and/or of the support. A preferred arrangement is that in which the encapsulated colour former is in the form of a layer on the back of a transfer sheet and the developer is in the form of a layer on the face of a receiver sheet.

Another arrangement of the components is that wherein the microcapsules which contain the colour former, and the developer, are in or on the same sheet, in the form of one or more individual layers, or are present in the paper pulp.

The capsules are preferably secured to the support by means of a suitable adhesive. As paper is the preferred support, these adhesives are principally paper-coating agents, for example gum arabic, polyvinyl alcohol, hydroxymethyl cellulose, casein, methyl cellulose, dextrin, starch or starch derivatives or polymer latices. These latter are e.g. butadiene/styrene copolymers or acrylic homopolymers or copolymers.

The paper employed comprises not only normal paper made from cellulose fibers, but also paper in which the cellulose fibres are replaced (partially or completely) by synthetic polymers.

The compounds of the formulae (1) to (5) can also be employed as colour formers in a thermoreactive recording material. This recording material usually contains at least one carrier, one colour former, one electron acceptor and, optionally, also a binder. Thermoreactive recording systems comprise, for example, heat-sensitive recording or copying materials or papers. These systems are used e.g. for recording information, for example in electronic computers, teleprinters or telewriters, or in recording and measuring instruments, e.g. electrocardiographs. The image (mark) formation can also be effected manually with a heated pen. Laser beams can also be used to produce heatinduced marks.

The thermoreactive recording material can be composed such that the colour former is dispersed or dissolved in one binder layer and the developer is dissolved or dispersed in the binder in a second layer.

Another possibility consists in dispersing both the colour former and the developer in one layer. Be means of heat the binder is softened at specific areas and the colour former comes into contact with the developer (electron acceptor) at those points where heat is applied and the desired colour develops at once.

Suitable developers are the same electron acceptors as are used in pressure-sensitive papers. Examples of developers are the clays already mentioned and especially phenolic resins, or also the phenolic compounds described e.g. in German Offenlegungsschrift No. 1 251 348, for example 4-tert-butylphenyl, 4-phenylphenol, 4-hydroxydiphenyl ether, α-naphtol, β-naphthol, 4-hydroxymethylbenzoate, 4-hydroxyacetophenone, 2,2'-dihydroxydiphenyl, 4,4-isopropylidenediphenol, 4,4'-isopropylidene-bis(2-methylphenol), 4,4'-bis(hydroxyphenyl)valeric acid, 2,2'-methylene-bis(4-phenylphenol), hydroquinone, pyrogallol, phloroglucinol, p-, m- and o-hydroxybenzoic acid, gallic acid, 1-hydroxy-2-naphthoic acid, as well as boric acid or organic, preferably aliphatic, dicarboxylic acids, for example tartaric acid, oxylic acid, maleic acid, citric acid, citraconic acid or succinic acid.

Fusible, film-forming binders are preferably used for the manufacture of the thermoreactive recording material. These binders are normally water-soluble, whereas the bisquinazolines and the developer are sparingly soluble or insoluble in water. The binder should be able to disperse and fix the colour former and the developer at room temperature.

By applying heat the binder softens or melts, so that the colour former comes in contact with the developer and a colour is able to form. Examples of binders which are soluble, or at least swellable, in water are e.g. hydrophilic polymers, for example polyvinyl alcohol, polyacrylic acid, hydroxyethylcellulose, methyl cellulose, carboxymethylcellulose, polyacrylamide, polyvinyl pyrrolidone, gelatin or starch.

If the colour former and the developer are in two separate layers, it is possible to use water-insoluble binders, i.e. binder which are soluble in non-polar or only weakly polar solvents, for example natural rubber, synthetic rubber, chlorinated rubber, alkyd resins, polystyrene, styrene/butadiene copolymers, polymethylacrylates, ethyl cellulose, nitrocellulose and polyvinyl carbazole. The preferred arrangement, however, is that in which the colour former and the developer are contained in one layer in a water-soluble binder.

The thermoreactive coatings may contain further ingredients. To improve the degree of whiteness, to facilitate the printing of papers, and to prevent the heated pen from sticking, the coatings may contain e.g. talcum, titanium dioxide, zinc oxide, aluminium hydroxide, calcium carbonate (e.g. chalk), clays or also organic pigments, for example urea/formaldehyde polymers. In order to effect the colour formation only within a limited temperature range, it is possible to add substances such as urea, thiourea, diphenyl thiourea, acetamide, acetanilide, stearyl amide, phthalic anhydride, metal stearates, phthalonitrile or other appropriate fusible products which induce the simultaneous melting of the colour former and the developer. Thermographic recording materials preferably contain waxes, e.g. carnauba wax, montan wax, paraffin wax or polyethylene wax.

The invention is illustrated by the following Examples, in which percentages are by weight, unless otherwise indicated.

EXAMPLE 1

26.5 g of the quinazolone of the formula

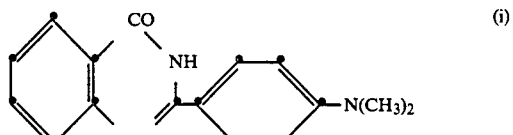

(m.p. 214–217° C.)

are dissolved in 150 g of 1,2-dichlorobenzene at 150° C. The solution is then cooled to 90° C. and 15.3 g of phosphoroxy chloride are added dropwise at 90°–95° C. over ½ hour. The reaction mixture is stirred for 1 hour at this temperatuure to give a dark red solution of the 4-chloro-2-(4'-dimethylaminophenyl)quinazoline of the formula

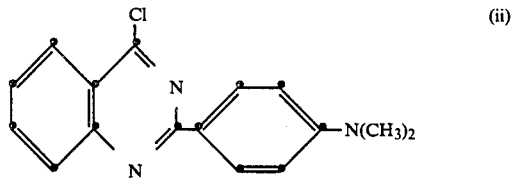

This solution is poured into a suspension of 11.4 g of 4,4'-isopropylidenediphenol (bisphenol A) and 2 g of tetrabutylammonium bromide in 64 g of 50% sodium hydroxide solution over the course of ½ hour. The reaction mixture is then refluxed for 1 hour, after which the dichlorobenzene is removed by steam distillation. The product precipitates in crystals, which are isolated by filtration at 50° C., washed with water and methanol and dried in vacuo at 80° C., affording 33.1 g of a bisquinazoline of the formula

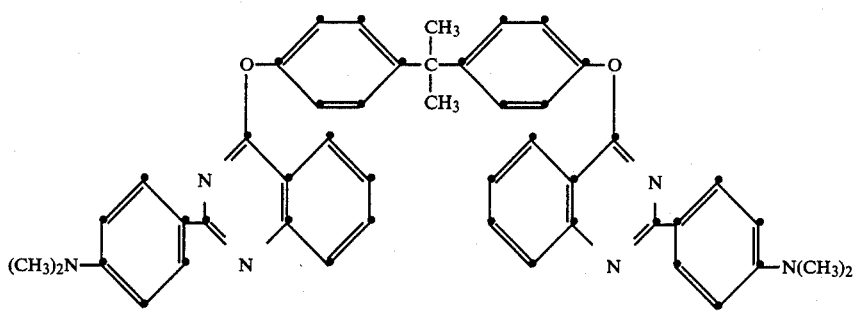
(21)

with a melting point of 204°–206° C.

The reflectance maximum of this bisquinazoline on paper coated with acid clay is in the range of 465 nm.

This colour former develops a yellow colour of excellent fastness of light and sublimation on acid clay.

EXAMPLE 2

The quinazolone of the formula (i) in Example 1 is replaced by 29.3 g of the quinazolone of the formula

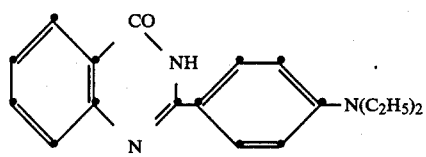
(iii)

and the same procedure is repeated, affording 34.2 g of a bisquinazoline of the formula

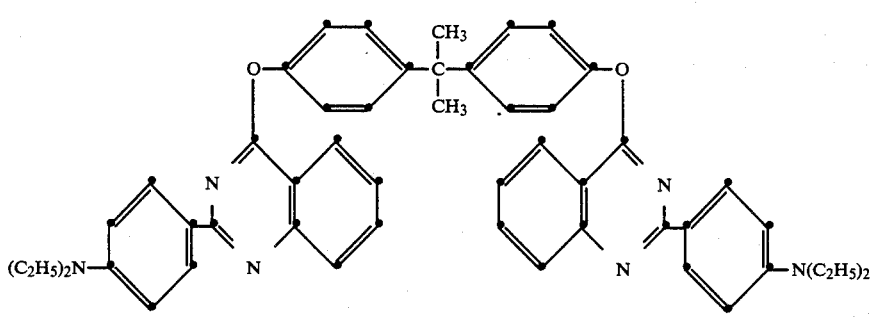
(22)

A sample recrystallised from toluene/methanol melts at 147°–150° C. The reflectance maximum on paper coated with acid clay is in the range of 470 nm.

This colour former develops a yellow colour of excellent fastness to light and sublimation on acid clay.

EXAMPLE 3

The isopropylidene compound employed in Example 1 is replaced by 19.2 g of a bisphenol compound of the formula

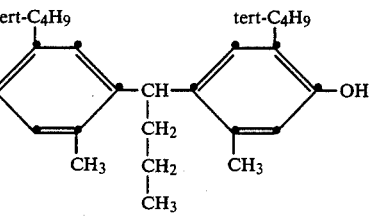

and the same procedure is repeated, affording 17.2 g of a bisquinazoline compound of the formula

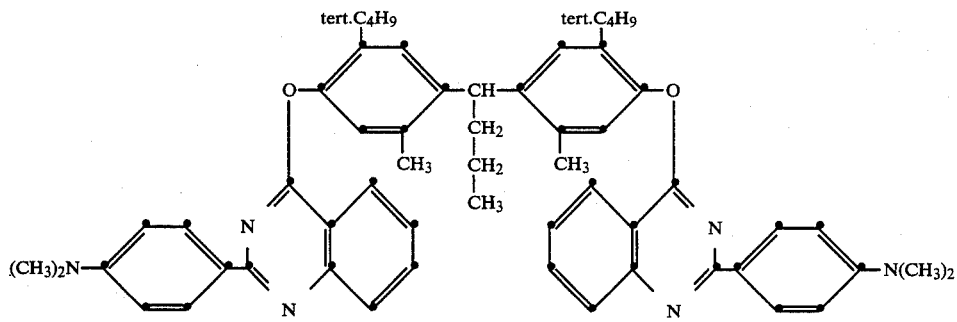
(23)

with a melting point of 145°–160° C.

The reflectance maximum on paper coated with acid clay is in the range of 465 nm.

This colour former develops a yellow colour of excellent fastness to light and sublimation on paper coated with acid clay.

The bisquinazolines of the formula (24)

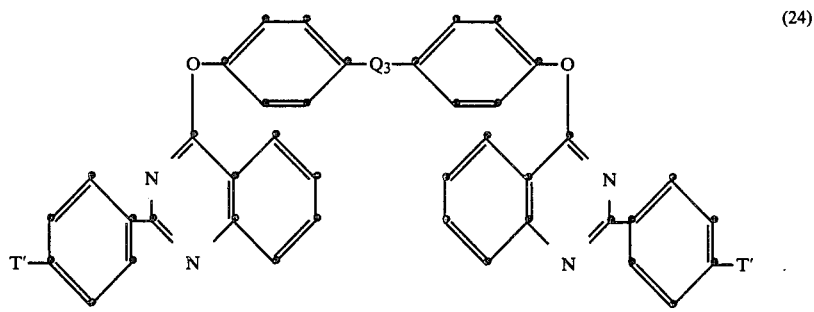

(24)

listed in the following table are obtained in the same manner as described in Examples 1 to 3, using the corresponding starting materials.

ture over 30 minutes. The reaction mixture is then stirred for 1 hour at 90°–95° C. The red solution of the 4-chloro-2-tetrahydroquinolinylquinazoline of the for-

TABLE

| Example | T' | $Q_3$ | m.p./°C. | Colour acid clay |
|---|---|---|---|---|
| 4 | —N(CH$_2$—Ph)$_2$ | isopropylidene | 60–70 | yellow |
| 5 | —N piperidine (H) | isopropylidene | 130–135 | yellow |
| 6 | —N(CH$_3$)—CH$_2$—Ph | isopropylidene | 119–123 | yellow |
| 7 | —N(n-C$_3$H$_7$)$_2$ | isopropylidene | 100–105 | yellow |
| 8 | —N(CH$_3$)(C$_2$H$_4$—CN) | isopropylidene | 70–80 | yellow |
| 9 | —N(CH$_3$)$_2$ | —CH$_2$— | 209–220 | yellow |
| 10 | —N(CH$_3$)$_2$ | cyclohexylidene | 216–225 | yellow |
| 11 | —N(phenyl)$_2$ | isopropylidene | 155–170 | yellow |

EXAMPLE 12

19 g of the quinazolone of the formula

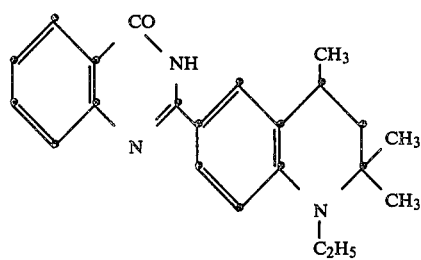

(iv)

are dissolved at 150° C. in 90 g of 1,2-dichlorobenzene. The solution is then cooled to 95° C. and 9 g of phosphoroxy chloride are added dropwise at this temperamula

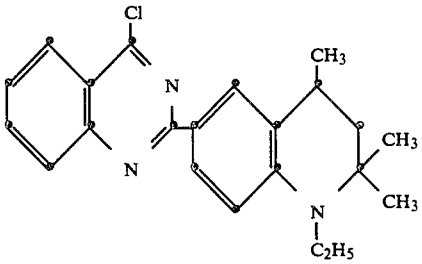

(v)

is poured over the course of 15 minutes into a suspension consisting of 11.4 g of 4,4'-isopropylidenediphenol, 2.2 g of tetrabutylammonium bromide and 35 g of a 50% aqueous solution of sodium hydroxide, whereupon the temperature rises to 110° C. The reaction mixture is stirred for 1 hour at 100°-110° C. and the 1,2-dichlorobenzene is removed by steam distillation. The precipitated product is dissolved in toluene with heating and the hot toluene solution is filtered over activated carbon. The product crystallises on cooling and the crystals are isolated by filtration and dried, affording 12 g of a compound of the formula

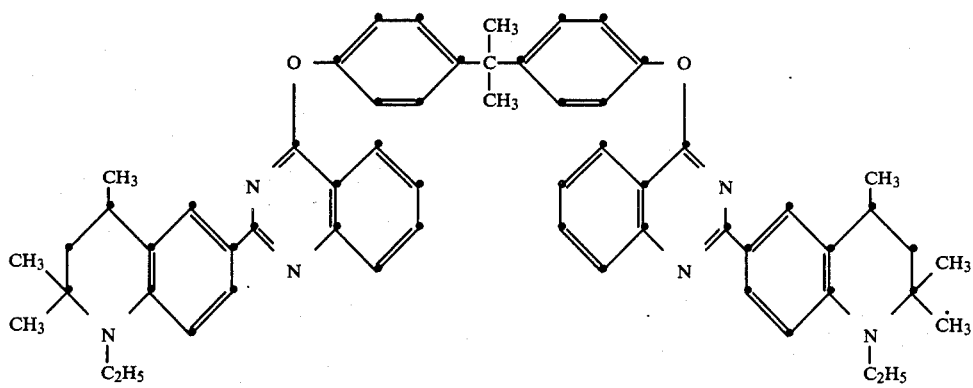

(25)

with a melting point of 193°-196° C.

This colour former develops a golden yellow colour of good fastness to light and sublimation on acid clay.

The quinazolone of the formula (iv) employed in Example 12 is prepared as follows:

23.1 g of N-ethyl-2,2,4-trimethyl-tetrahydroquinoline-6-aldehyde are dissolved in 150 ml of ethanol. To this solution are added 13.6 g of anthranilamide and 4 ml of 10% sulfuric acid and the reaction mixture is heated to 60° C. The mixture is kept for 1 hour at 60° C. and the product is oxidised by the dropwise addition of 69 g of a 40% aqueous solution of sodium bisulfite and then stirring the reaction mixture for 2 hours at reflux temperature. After cooling to room temperature, the precipitated product is isolated by filtration, washed with ethanol and dried, affording 19 g of the quinazolone of the formula (iv) with a melting point of 215°-219° C.

EXAMPLE 13

Preparation of a pressure-sensitive copying paper

A solution of 3 g of the bisquinazoline of the formula (21) in 80 g of diisopropylnaphthalene and 17 g of kerosene are microencapsulated by coacervation in a manner known per se with gelatin and gum arabic. The microcapsules are mixed with starch solution and coated on a sheet of paper. The face of a second sheet of paper is coated with acid-activated bentonite as colour developer. The first sheet and the sheet coated with the developer are laid on top of each other with the coated sides face to face. Pressure is exerted on the first sheet by writing by hand or typewriter and an intense yellow copy of excellent lightfastness develops immediately on the sheet coated with the developer.

Corresponding intense yellow copies which are fast to sublimation and light are also obtained using each of the other colour formers of the formulae (22) to (25) as indicated in the Preparatory Examples.

EXAMPLE 14

The procedure of Example 13 is repeated, replacing the bisquinazoline of the formula (21) by a mixture of the following composition: 1.2 g of 3,3-bis-(4'-dimethylaminophenyl)-6-dimethylaminophthalide, 1.2 g of N-butylcarbazol-3-yl-bis-(4'-N-methyl-N-phenylaminophenyl)methane, 1.5 g of the bisquinazoline of the formula (21) and 0.4 g of 3,3-bis-(N-n-octyl-2'-methylindol-3'-yl)phthalide. The so obtained pressure-sensitive recording material gives an intense and lightfast black copy when pressure is exerted by hand or typewriter.

EXAMPLE 15

1 g of the bisquinazoline of the formula (22) is dissolved in 17 g of toluene. With stirring, 12 g of polyvinyl acetate, 8 g of calcium carbonate and 2 g of titanium dioxide are added to this solution. The resultant suspension is diluted with toluene in the weight ratio 1:1 and coated on a sheet of paper with a knife to a thickness of 10 μm. On this sheet of paper is laid a second sheet, the underside of which has been coated to a weight of 3 g/m² with a mixture consisting of 1 part of an amide wax, 1 part of a stearin wax and 1 part of zinc chloride. Pressure is exerted on the top sheet by hand or typewriter and an intense yellow colour which is fast to sublimation and light develops immediately on the sheet coated with the colour former.

EXAMPLE 16

Preparation of a heat-sensitive recording material

In a ball mill, 32 g of 4,4'-isopropylidenediphenol (bisphenol A), 3.8 g of the distearylamide of ethylenediamine, 38 g of kaolin, 20 g of an 88% hydrolysed polyvinyl alcohol and 500 ml of water are ground to particle size of about 5 μm. In a second ball mill, 6 g of the bisquinazoline of the formula (21), 3 g of an 88% hydrolysed polyvinyl alcohol and 60 ml of water are ground to particle size of about 3 μm.

Both dispersions are mixed and coated on paper to a dry coating weight of 5.5 g/m². An intense yellow colour of excellent fastness to light and sublimation is produced by contacting the paper with a heated ballpoint pen. Intense and lightfast yellow colours can also be obtained using each of the other colour formers of the formulae (22) to (25).

EXAMPLE 17

In a ball mill, 2.7 g of the bisquinazoline of the formula (22), 24 g of N-phenyl-N'-(1-hydroxy-2,2,2-trichloroethyl)-urea, 16 g of stearylamide, 59 g of an 88% hydrolysed polyvinyl alcohol and 58 ml of water are ground to a particle size of 2–5 μm. This suspension is coated on a sheet of paper to a dry coating weight of 5.5 g/m². An intense yellow which is fast to sublimation and light is obtained by contacting the paper with a heated ball-point pen.

What is claimed is:

1. A pressure sensitive or heat-sensitive recording material which comprises a support which contains, or has coated thereon, as a color former, at least one bisquinazoline of the formula

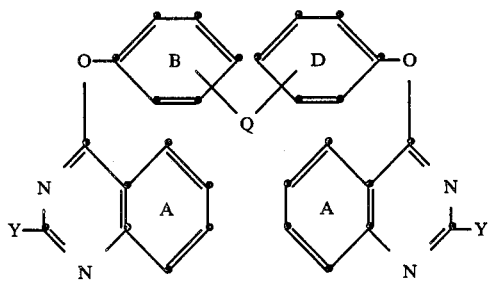

wherein
Q is the direct bond, an aliphatic or cycloaliphatic hydrocarbon radical containing not more than 8 carbon atoms, or is —CO—, —S— or —SO₂—, and
Y is the radical of a couplable compound selected from the group consisting of unsubstituted or N-monosubstituted or N,N-disubstituted anilines or naphthylamines, N-unsubstituted or N-substituted indoles, indolines, carbazoles, tetrahydrocarbazoles, dihydroquinolines, tetrahydroquinolines, dibenzylimides, benzomorpholines or phenylpyrazolines, and the rings
A, B and D each independently are unsubstituted or substituted by cyano, nitro, halogen, lower alkyl, phenyl, benzyl, lower alkoxy or lower alkoxycarbonyl.

2. A recording material according to claim 1 wherein Y is a radical of the formula

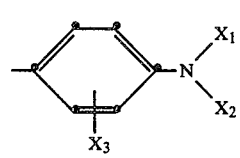

(2a)

or the radical of the formula

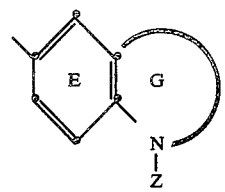

wherein $X_1$ and $X_2$ are each independently hydrogen, $C_1$–$C_{12}$alkyl which is unsubstituted or substituted by halogen, hydroxy, cyano or lower alkoxy, or are cycloalkyl, phenyl, benzyl, or phenyl or benzyl each substituted by halogen, nitro, cyano, lower alkyl, lower alkoxy or lower alkoxycarbonyl or $X_1$ and $X_2$, together with the nitrogen atom to which they are attached, are a 5- or 6-membered heterocyclic radical, $X_3$ is hydrogen, halogen, nitro, lower alkyl, lower alkoxy or lower alkoxycarbonyl, and Z is hydrogen or $C_1$–$C_8$alkyl which is unsubstituted or substituted by halogen, cyano or lower alkoxy, or is cycloalkyl or benzyl, and the ring E is unsubstituted or substituted by cyano, halogen, lower alkyl or lower alkoxy, and the ring G is a hydrogenated 5- or 6-membered N-heterocyclic ring system which is unsubstituted or C-substituted by one or more than one of the same or different substituents selected from the group consisting of halogen, cyano, hydroxyl, lower alkyl, lower alkoxy, $C_5$–$C_6$cycloalkyl, benzyl or $C_3$–$C_6$alkylene.

3. A recording material according to claim 2 wherein Y is a radical of the formula (2a).

4. A recording material according to claim 3 wherein $X_1$ and $X_2$ are each independently lower alkyl, benzyl, phenyl, lower alkylphenyl or lower alkoxyphenyl.

5. A recording material according to claim 2 wherein Y is a radical of the formula (2b) and ring G is a 6-membered N-heterocyclic ring system.

6. A recording material according to claim 2 wherein Y is a radical of the formula (2b) and Z is lower alkyl, benzyl, or beta-cyanoethyl.

7. A recording material according to claim 1 wherein Q is an aliphatic hydrocarbon radical containing up to 8 carbon atoms or a cycloaliphatic hydrocarbon radical containing 5–7 carbon atoms in the ring which may contain one or two methyl groups on the ring.

8. A recording material according to claim 1, wherein Q is bonded to rings B and D in the para position on each with respect to the oxygen atoms.

9. A pressure-sensitive or heat-sensitive recording material which comprises a support which contains, or has coated thereon, as a color former, at least one bisquinazoline of the formula

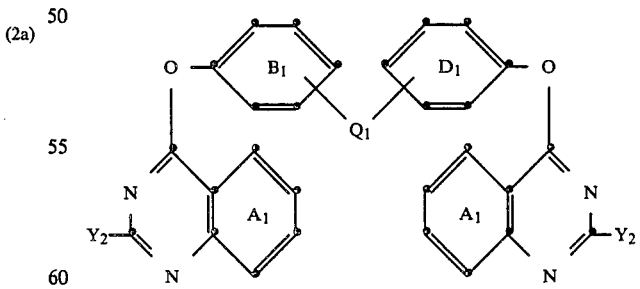

wherein $Q_1$ is the direct bond, a straight chain or branched alkylene or alkylidene radical, each containing not more than 8 carbon atoms, or is a cyclohexylidene radical, $Y_2$ is
an aminophenyl radical of the formula

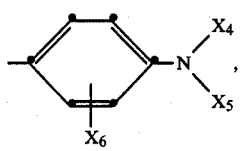

a 5-indoline radical of the formula

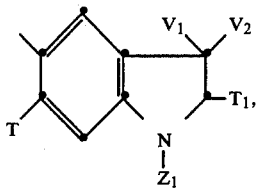

a tetrahydroquinolinyl radical of the formula

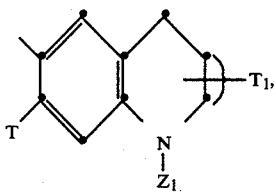

a tetrahydroquinolinyl radical of the formula

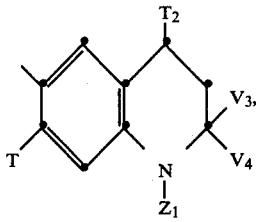

or a benzomorpholino radical of the formula

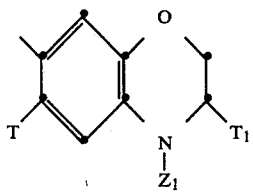

in which formulae $X_4$ and $X_5$ are each independently lower alkyl, cyano-lower alkyl, benzyl, phenyl, lower alkylphenyl or lower alkoxyphenyl, or $X_4$ and $X_5$, together with the nitrogen atom to which they are attached, are pyrrolidino, piperidino or morpholino, $X_6$ is hydrogen, halogen, lower alkyl or lower alkoxy, $Z_1$ is hydrogen, $C_1-C_8$alkyl, $C_2-C_6$alkoxyalkyl, $\beta$-cyanoethyl or benzyl, T is hydrogen, halogen, lower alkyl, lower alkoxy, $C_1-C_4$acylamino or phenyl, $T_1$ and $T_2$ are each hydrogen, halogen, hydroxy, lower alkyl or lower alkoxy, and $V_1$, $V_2$, $V_3$ and $V_4$ are each hydrogen, lower alkyl, cycloalkyl or benzyl, or ($V_1$ and $V_2$) or ($V_3$ and $V_4$) are each together alkylene, and the rings $A_1$, $B_1$ and $D_1$ are each independently unsubstituted or substituted by one or two members of the group selected from cyano, halogen, lower alkyl, phenyl and lower alkoxy.

10. A recording material according to claim 9 wherein $Y_2$ is a radical of the formula (3a).

11. A recording material according to claim 10 wherein $X_4$ and $X_5$ are each lower alkyl or benzyl and $X_6$ is hydrogen.

12. A recording material according to claim 9 wherein $Q_1$ is $C_1-C_4$-alkylene or $C_2-C_4$-alkylidene.

13. A recording material according to claim 9 wherein ring $A_1$ is unsubstituted and rings $B_1$ and $D_1$ are unsubstituted or substituted by one or two substituents selected from methyl and tert.-butyl.

14. A recording material according to claim 9 wherein $Y_2$ is a radical of formula (3d).

15. A recording material according to claim 9 wherein $Y_2$ is a radical of formula (3e).

16. A recording material according to claim 15 wherein $Z_1$ is benzyl, beta-cyanoethyl or $C_1-C_8$-alkyl.

17. The pressure-sensitive recording material of claim 9 wherein the bisquinazoline is dissolved in an organic solvent, and which recording material further comprises at least one solid electron acceptor.

18. The pressure-sensitive recording material of claim 17, wherein the bisquinazoline is encapsulated in microcapsules.

19. The pressure-sensitive recording material of claim 18, wherein the encapsulated bisquinazoline is present in the form of a layer on the back of transfer and the electron acceptor is present in the form of a layer on the face of a receiver sheet.

20. The pressure-sensitive recording material of claim 9, which comprises the bisquinazoline together with one or more other color formers.

21. The heat-sensitive recording material of claim 9, which comprises in at least one layer, at least one bisquinazoline color former, at least one electron acceptor and at least one binder.

22. A pressure-sensitive or heat-sensitive recording material which comprises a support which contains, or has coated thereon, as a color former, at least one bisquinazoline of the formula

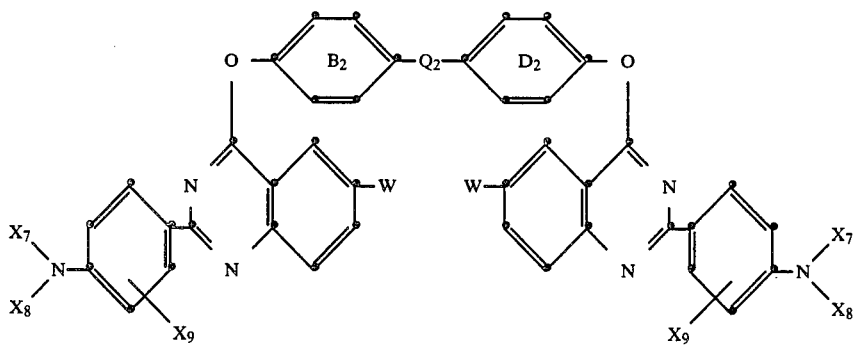

wherein
Q$_2$ is straight chain or branched alkylene or alkylidene each of at most 4 carbon atoms, or cyclohexylidene,
X$_7$ and X$_8$ are each lower alkyl, β-cyanoethyl, benzyl or phenyl, or —NX$_7$X$_8$ is piperidino,
X$_9$ is hydrogen, methyl, methoxy or ethoxy,
W is hydrogen, halogen, methyl or methoxy
and the rings B$_2$ and D$_2$ are unsubstituted by one or two substituents selected from methyl, methoxy and tert-butyl.

23. A recording material according to claim 22 wherein each of the rings B$_2$ and D$_2$ is unsubstituted or substituted by methyl or tert-butyl.

24. A pressure-sensitive or heat-sensitive recording material which comprises a support which contains, or has coated thereon, as a color former, at least one bis-quinazoline of the formula

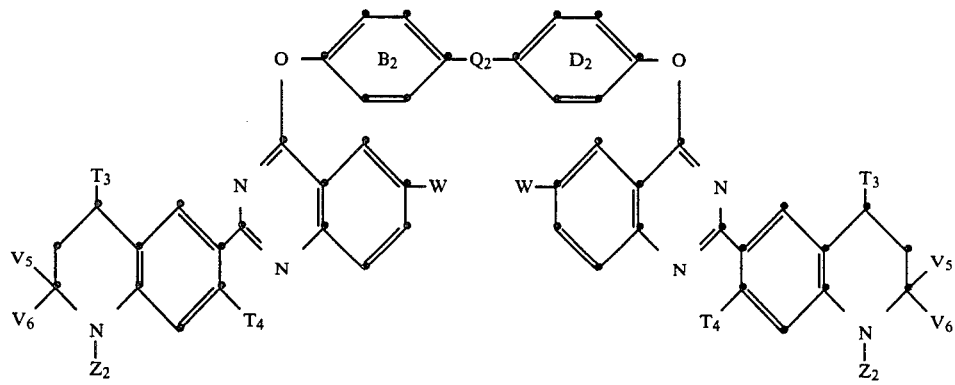

wherein
Q$_2$ is straight chain or branched alkylene or alkylidene each containing at most 4 carbon atoms,
Z$_2$ is C$_4$–C$_8$alkyl, β-cyanoethyl or benzyl,
T$_3$, V$_5$ and V$_6$ are each lower alkyl,
T$_4$ is hydrogen or methyl, and
W is hydrogen, halogen, methyl or methoxy,
and the rings B$_2$ and D$_2$ are unsubstituted or substituted by one or two substituents selected from methyl, methoxy and tert-butyl.

* * * * *